United States Patent
Poulsen

(10) Patent No.: US 6,858,023 B2
(45) Date of Patent: Feb. 22, 2005

(54) REUSABLE COLLECTING BAG FOR HUMAN BODY WASTES

(75) Inventor: Lars Bo Poulsen, Helsingør (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 10/344,410

(22) PCT Filed: Aug. 14, 2001

(86) PCT No.: PCT/DK01/00538
§ 371 (c)(1),
(2), (4) Date: Feb. 14, 2003

(87) PCT Pub. No.: WO02/13737
PCT Pub. Date: Feb. 21, 2002

(65) Prior Publication Data
US 2003/0167042 A1 Sep. 4, 2003

(30) Foreign Application Priority Data
Aug. 15, 2000 (DK) .......................................... 2000 01213

(51) Int. Cl.[7] .................................................. A61F 5/44
(52) U.S. Cl. ...................................... 604/335; 604/332
(58) Field of Search ............................... 604/335–342, 604/355, 332

(56) References Cited

U.S. PATENT DOCUMENTS

| 4,460,359 A | 7/1984 | Fenton |
| 4,753,703 A | 6/1988 | Jensen |
| 4,988,343 A | 1/1991 | Ballan |
| 5,968,024 A | 10/1999 | Freeman |

FOREIGN PATENT DOCUMENTS

| EP | 0276042 | 7/1988 |
| GB | 2000683 | 1/1979 |
| GB | 2268065 | 1/1994 |
| WO | WO 96/19164 | 6/1996 |
| WO | WO 99/25278 | 5/1999 |
| WO | WO 99/66859 | 12/1999 |

Primary Examiner—Larry I. Schwartz
Assistant Examiner—Michele Kidwell
(74) Attorney, Agent, or Firm—Jacobson Holman PLLC

(57) ABSTRACT

In a reusable collecting bag such as a stoma bag (1) having a narrowed discharge portion (8) including a slit-like discharge opening in the vicinity of its distal end the discharge portion (8) is brought from an open position for emptying the bag through the discharge opening (9) and a closed position of use by folding and unfolding the discharge portion (8) about at least one folding line (24) transverse to the longitudinal direction of the discharge portion (8). To avoid or reduce faecal contamination of the discharge portion (8) in connection with emptying of the bag a series (16, 18) of sequentially peelable stacked protective members (17, 19) is applied to each of two surface sections of the discharge portion (8) adjacent the discharge opening (9).

16 Claims, 6 Drawing Sheets

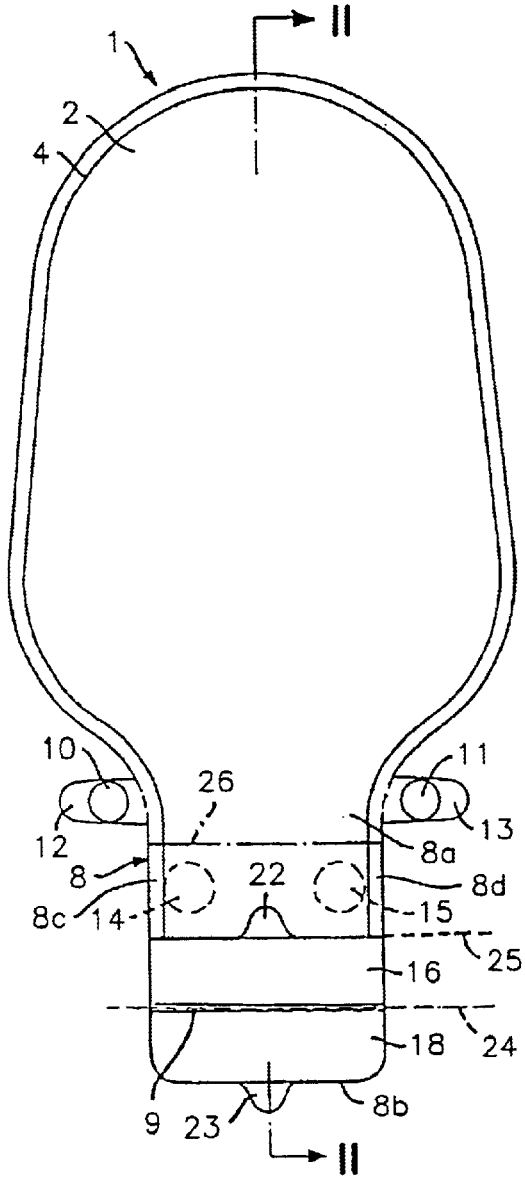
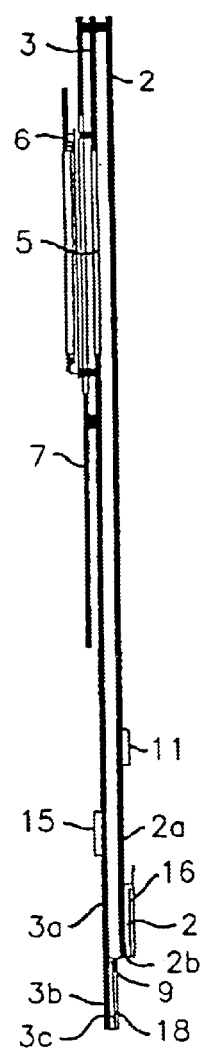
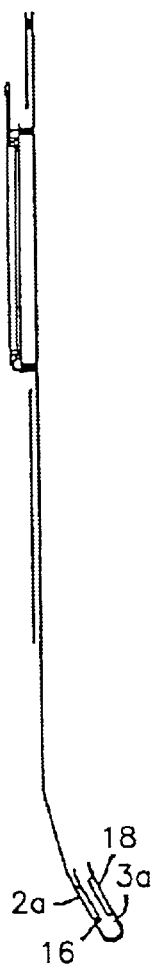

FIG. 5
FIG. 4
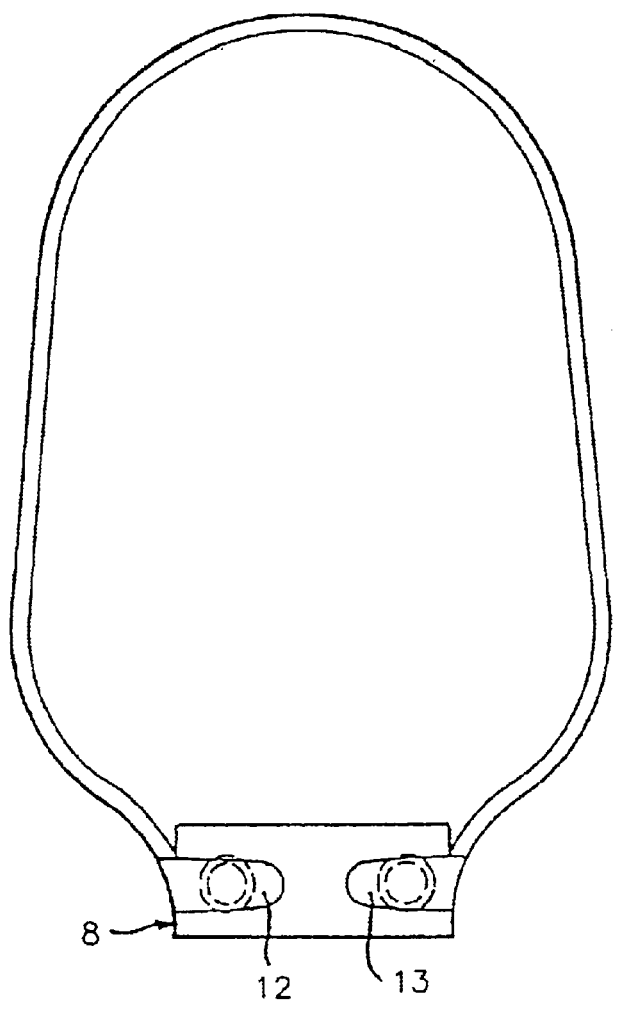
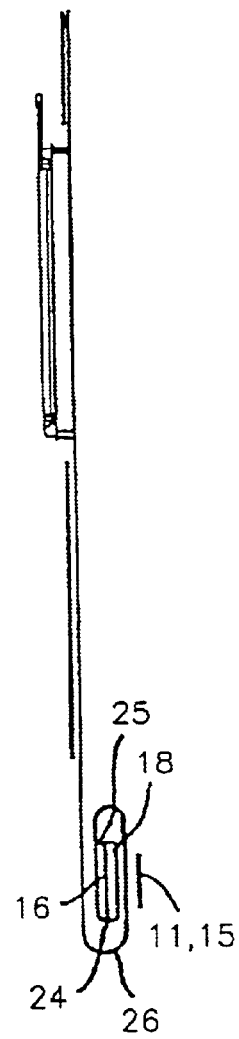

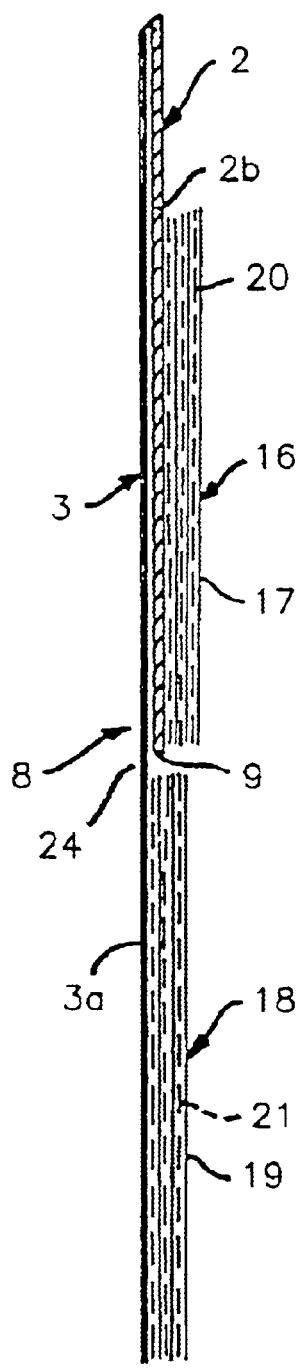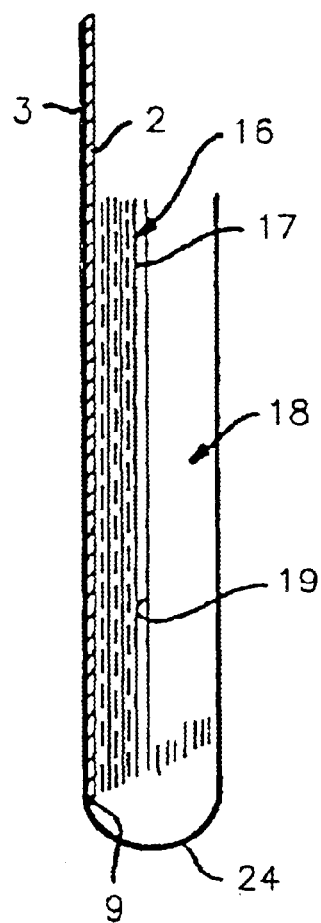

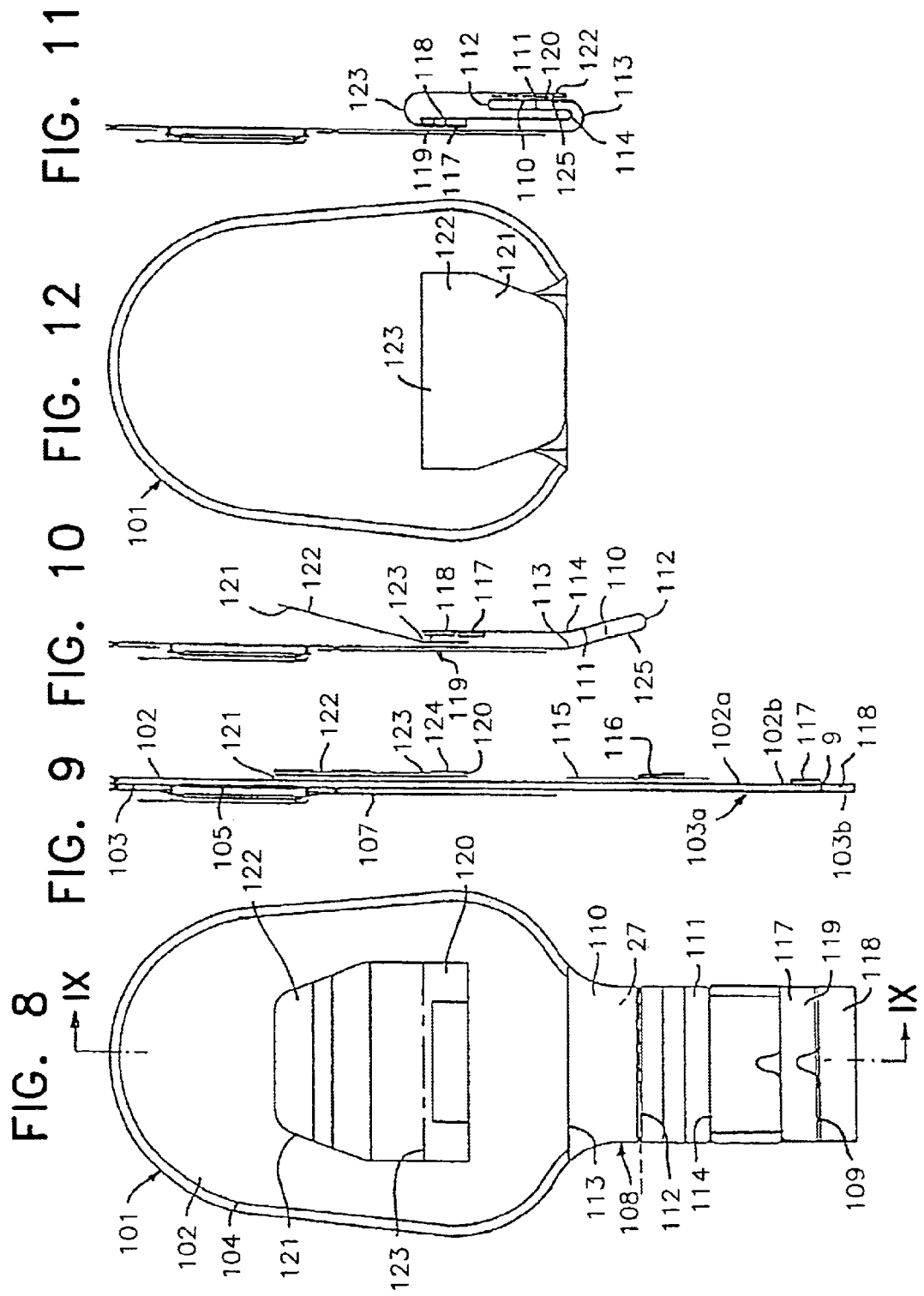

REUSABLE COLLECTING BAG FOR HUMAN BODY WASTES

This is a nationalization of PCT/DK01/00538 filed Aug. 14, 2001 and published in English).

BACKGROUND OF THE INVENTION

1. Field of the Invention

The invention relates to a reusable collecting bag for human body wastes comprising a bag member formed by two film blanks with joined edges, an inlet opening provided in one of said film blanks, connecting elements surrounding said inlet opening for connection of the bag to a body orifice, a narrowed, elongated discharge portion starting at a proximal end at a distance from the inlet opening and extending between two end sections of said film blanks to a distal end, a discharge opening formed in said discharge portion in the vicinity of said distal end, said discharge portion being foldable and unfoldable by at least one folding along a folding line transverse to the longitudinal direction of the discharge portion between said distal and proximal ends to bring the discharge portion from an open unfolded condition to a closed folded condition and vice versa, and a locking device being provided at the discharge portion for locking the bag in said closed folded condition of the discharge portion.

2. Description of the Related Art

This type of drainable collecting bags are often used as ostomy bags. In the case of ileostomy patients and colostomy patients with uncontrolled release of faeces of a more or less fluid consistence, the collecting bag has to be emptied rather frequently, and the discharge portion thus has to be easy to open and re-close after emptying and at the same time provide a reliable and tight seal in operation, ie. between emptyings.

Several different designs of closure devices have been developed and are generally known.

For instance, GB patent applications Nos. 2 268 065 and 2 000 683 disclose collecting bag with closure devices, in which strips of the interlocking-elements type, such as Velcro®, are placed on each of the film blanks of the discharge portion and which after folding the discharge portion tightly are brought into contact with each other.

Further designs are shown in EP patent application No. 0 013 109, in which the outlet portion is folded and subsequently tucked into a gap formed by a semi-rigid strip attached to the bag wall, as well as published international patent application WO 99/25278, in which the locking means comprises an adhesive layer applied to at least one of two contact surfaces on the discharge portion designed to be brought into contact with each other upon folding of the discharge portion towards the closed position.

Other types of closure device are disclosed in U.S. Pat. No. 4,988,343 and published international patent applications Nos. WO 96/19164 and WO 99/66859, in which the discharge portion is rolled up on a locking clip fastened to one of the film blanks.

All of the above-mentioned prior art devices suffer, however, from the common disadvantage that at each emptying or discharge of the faecal or urine content of the bag contamination of the surface parts of the discharge portion adjacent to the discharge opening is hardly avoidable and that consequently washing or cleaning of such surface parts is necessary prior to reclosing of the discharge portion. Evidently such a cleaning operation is not only highly inconvenient and unpleasant to perform, but makes the handling of the bag cumbersome and causes severe problems in particular for users having reduced dexterity.

SUMMARY OF THE INVENTION

On this background, it is the object of the present invention to provide a reusable collecting bag of the kind defined, by which the drawback and handling inconvenience of the prior art devices has been eliminated or at least significantly reduced.

According to the invention, this object is achieved by a reusable collecting bag of the kind defined, which is characterized in that a series of stacked, sequentially peelable adhesive protective members is applied to each of two surface sections of the discharge portion at either side of the discharge opening.

By covering the surface sections of the discharge portion adjacent to the discharge opening with such series of stacked, sequentially peelable protective members the contamination resulting from emptying the bag may be easily removed by peeling off the outermost of the stacked protective members to expose a non-contaminated surface area adjacent to the discharge opening.

Preferred and advantageous embodiments of the reusable collecting bag are stated in the dependent claims.

As will appear therefrom and from the following description the series of peelable protective members according to the invention may be applied to different designs of the bag discharge portion with different locations of the discharge opening and different forms and locations of the locking means.

By itself the application of a series of stacked sequentially peelable, adhesive members to a surface part of a reusable article is known in the art, e.g. from EP patent No. 0 276 043 disclosing the application of such an arrangement of adhesive devices to the attachment of an ostomy bag to a body-attachable pad.

BRIEF DESCRIPTION OF THE DRAWINGS

In the following the invention will be described in further detail with reference to the schematic drawings, in which FIG. 1 shows a plan view of an embodiment of a reusable collecting bag according to the invention, seen from the side intended to face away from the user and in the fully open position;

FIG. 2 shows a longitudinal section of the collecting bag along the line II—II in FIG. 1;

FIG. 3 is a schematic side view diagram of the collecting bag in an intermediate position showing only relevant parts of the bag;

FIG. 4 is a view corresponding to FIG. 1 in the fully closed position of the bag;

FIG. 5 is a diagram corresponding to FIG. 3 of the collecting bag in the fully closed position;

FIGS. 6 and 7 are enlarged schematical cross-sectional views of a distal end part of a discharge portion of the bag in an open and closed condition, respectively;

FIGS. 8 to 12 are views corresponding to FIGS. 1 to 4 of a modification of the discharge portion of the collecting bag in FIG. 1.

In FIGS. 2, 3, 4, 9, 10 and 11 some sectional areas are indicated by fully drawn lines in order not to impede the clear reading of the drawings.

DETAILED DESCRIPTION OF THE PREFERRED EMBODIMENTS

Figure 13:
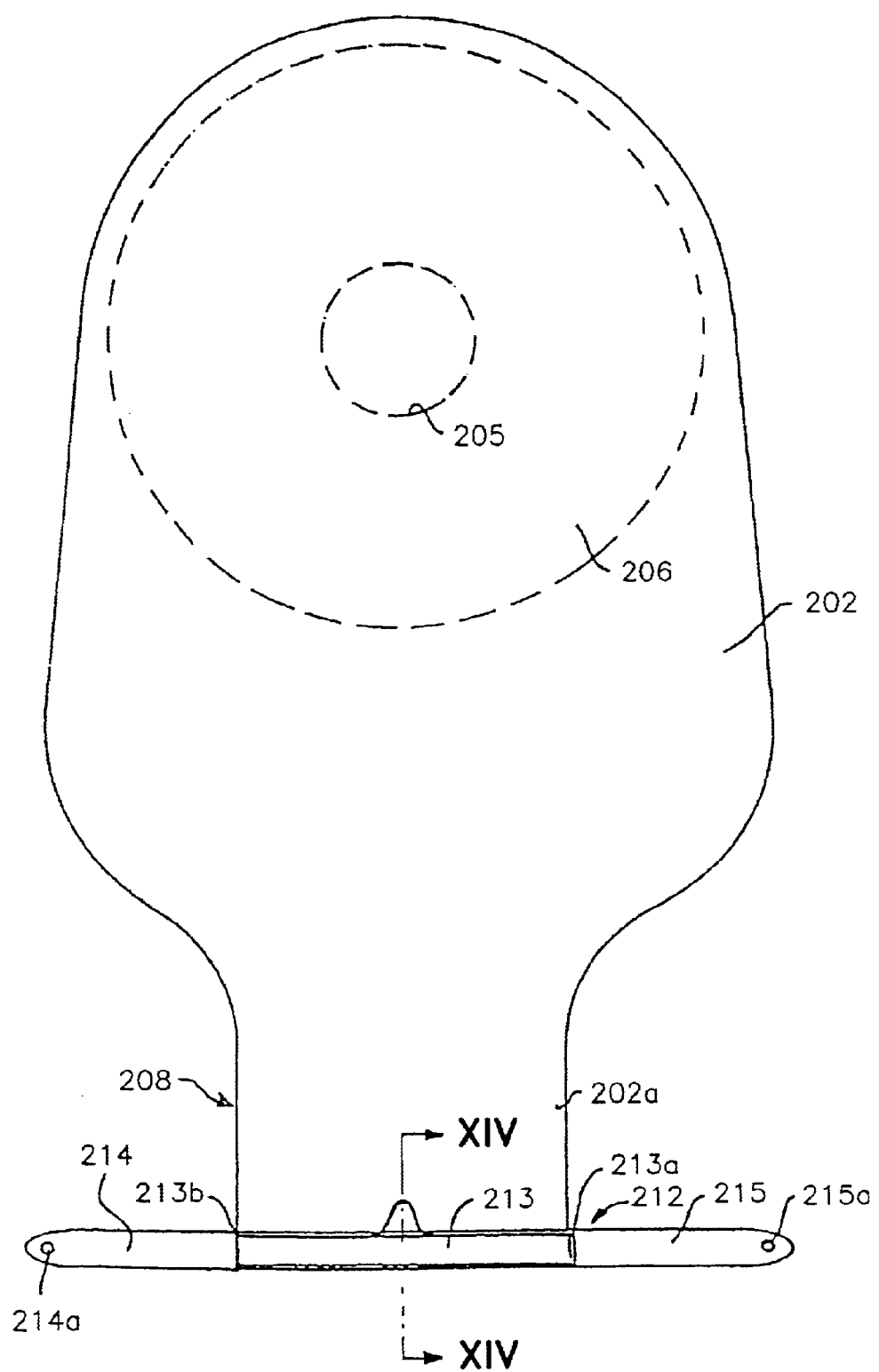
FIGS. 13 to 15 are views partly corresponding to FIGS. 1. 2 and 4 of a further embodiment.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The collecting bag shown in the drawings is designed as an ostomy bag of a generally known and common type and comprises a bag member 1 formed by two film blanks 2,3 which are joined along their edges by means of a seam 4 made by welding or in any other convenient manner. The film blanks may be made from any suitable flexible plastic sheet or foil material.

In the film blank 3, which in use is intended to face the user and thus forms the back wall of the bag, an inlet opening 5 is provided, which in a manner known per se is surrounded by connecting elements 6 for connection of the bag to a body orifice, ie. in this case an intestinal orifice in the form of a so-called stoma in the user's abdominal wall.

As seen in FIG. 2 a comfort layer 7 of another material than the one used for the film blanks may be provided on the back film blank 3. As further explained in the following both of the two film blanks may alternatively be provided with such a comfort layer which may be made of a conventional non-woven tissue material.

At a distance from the inlet opening 5, the bag is designed with a narrowed, elongated discharge portion 8 starting at a proximal or neck end 8a and extending to a distal or terminal end 8b. The discharge portion 8 is formed by end sections 2a and 3a, respectively, of the film blanks 2,3 and is likewise joined along opposed side edges 8c and 8d.

A short distance from the distal end 8b of the discharge portion 8, a discharge opening 9, through which the bag may be emptied of its contents, is formed as a slit between the distal end edge of the end section 2a of the front film blank 2 and an extreme end part 3b of the end section 3a of the back film blank 3 as further explained in the following.

In order to bring the bag from the open or discharge position shown in FIGS. 1 and 2 to a position of use, in which the bag is closed, the collecting bag comprises locking means, which in the embodiment shown comprises foldable locking strips 12 and 13 projecting from the side edges 8c and 8d of the discharge portion 8 at the proximal end 8a thereof. The projecting foldable locking strips 12 and 13, which may be formed integrally with one of the film blanks 2,3, may comprise male snap fastening members, VELCRO® closure members, different types of adhesive members etc. and are realisably engageable with a second mating locking means 14 and 15 provided on the back film blank 3. It should be noted that the locking device may be designed in other ways, e.g. as a traditional locking clip.

In the embodiment shown in FIGS. 1 to 5, a first series 16 of stacked, sequentially peelable adhesive protective members 17 is applied to the surface of the extreme end part 2b of the end section 2a of the front film blank 2 immediately adjacent the end edge of end section 2a limiting the discharge opening 9. Likewise a second series 18 of stacked, sequentially peelable adhesive protective members 19 is applied to the surface of the extreme end part 3b of the end section 3a of the back film blank 3. Resilient sealing plates 2c, 3c may be provided on the discharge portion to improve sealing thereof.

In the illustrated embodiment, each series 16 and 18 of protective members includes, as more clearly shown in FIGS. 6 and 7, three stacked strip or tape like members 17 and 19, respectively, held together by intermediate layers 20 and 21, respectively, of an adhesive permitting easy sequential peel-off of a single protective member at a time.

The protective strip or tape members 17 and 19 may be made of any suitable material known in the art for removable surface protective members. A preferred material would be a plastic film material providing sufficient protective sealing against penetration of faecal contamination, such as polyethylene or polypropylene. In a further preferred embodiment the protective strip or tape members are made from materials, which are water soluble or easily degradable, such that protective members peeled off from the bag can be easily disposed of, e.g. by being thrown into a toilet, without presenting any environmental problem. Such protective members could be composed e.g. of an easily degradable non-woven sheet material such as sanitary paper with a water soluble adhesive applied to the side contacting an underlying protective member and a thin sealing layer applied to the external side.

To allow easy peeling-off of the outermost protective member 17 or 19 in each of series 16 and 18, each of the stacked protective members 17 and 19 may, as shown in FIG. 1, be provided with a gripping flap 22 and 23, respectively. In the embodiment shown in FIG. 1 the gripping flaps project beyond the side edges of the projective members 17 and 19, which are parallel to the discharge slit 9, so as not to impede with the locking function of strips 12 and 13, but they may also be provided at other side edges of the protective members.

The sequence of operations required to bring the collecting bag from the open discharge position shown in FIG. 1 towards the fully closed position of use is illustrated in FIGS. 2 to 5.

Although the application of the series 16 and 18 of protective members may add some increased rigidity to the extreme end parts 2b and 3b, respectively, of end sections 2a and 3a, the first step will as illustrated in FIGS. 2 and 3 comprise folding of the extreme end part 3b of end section 3a about a folding line 24, which in this case coincides with the discharge slit 9 in a direction such that the series 16 and 18 of protective members 17 and 19 face each other. Subsequently, the thus folded end parts 2b and 3b may be folded, as illustrated in FIG. 4 by two subsequent foldings about second folding lines 25 and 26 to bring the discharge portion 8 to a completely folded position permitting locking of the bag in the closed position by engagement of locking strips 12 and 13 with locking means 14 and 15 as shown in FIG. 5.

When emptying of the bag is required, the sequence of operations needed to bring the bag from the closed position of use shown in FIG. 5 to the open discharge position shown in FIG. 1 is the opposite. After release of the engagement between locking strips 12, 13 and locking means 14, 15 the discharge portion 8 is unfolded and the faecal content of the bag is emptied through the discharge opening 9. After emptying the bag the outermost protective strip member 17 and 19 in each of series 16 and 18 is peeled-off to expose the clean surfaces of the underlying strips 17 and 19 adjacent to the discharge opening, before the discharge portion 8 is folded back towards its closed position.

The number of protective members in each of series 16 and 18 will thus depend on the envisaged number of reuses of the bag. Typically, a number of stacked members will be provided in each of series 16 and 18, which will allow 24 hours use of the bag without replacement, e.g. from 3 to 5 stacked members, whereas in order to avoid difficulties in handling of the discharge portion in connection with the unfolding and unfolding thereof, the number would preferably not increase eight stacked members, In the embodiment illustrated in FIGS. 8 to 12 the collection part of the bag is, in principle, of he same design as shown in FIG. 1 to 5 and only the discharge portion 27 and the folding and unfolding thereof for closing and opening of the bag will be further described.

Also in this case, the discharge portion 108 comprises a number of foldable sections. At the proximal end of the discharge portion 108 foldable sections 110 and 111 are formed, of which the former is arranged between two folding lines 112 and 113 and the latter between folding line 112 and a limiting line 114. The foldable sections 110 and 111 are provided with a carrier plate 115, typically made of a foam material, which is fastened to the front film blank 102.

As illustrated in FIGS. 9 and 10, in a first folding step during closing of the bag the discharge portion 108 is folded about folding line 112 to bring the surface parts of the carrier plate 115 fastened to sections 110 and 111, respectively, into mutual surface contact. To hold the discharge portion 108 in this first folded position, one of the surface parts of the carrier plate 115, e.g. the surface part applied to section 111 is provided with a layer 116 of an adhesive capable of easy release and repeated adhesion.

In the discharge portion 108 the discharge opening 109 is provided in the same way as described for the embodiment in FIGS. 1 to 5 as a slit-like opening between the end edge of an extension 102a of front film blank 102 and an extreme end part 103b of an extension 103a of the back film blank 103. On either side of the slit-like discharge opening 109 first and second series 117 and 118 of stacked, sequentially peelable adhesive protective members are applied to the extreme ends part 102b and 103b, respectively, of the extensions 102a and 103a of the front and back film blanks. The two series 117 and 118 of protective members may, in principle be designed and composed as described above for the embodiment in FIGS. 1 to 5.

As illustrated in FIG. 10 the extreme end parts 102b and 103b of the film blank extension 102a and 103a are, in this case not folded with respect to each other, but provide a contact surface 119 for use in a subsequent folding operation, in which the distal end of the discharge portion 108 comprising the extreme end parts 102b and 103b is folded, as shown in FIG. 11, about the folding line 114 in the same folding direction as the first folding about folding line 112.

By this subsequent folding the contact surface 119 provided by the outermost protective member in series 117 and 118 is brought into contact with a contact surface 120 provided by a flap element 121 fastened to the front film blank 102 and comprising a flexible flap portion 122, which is foldable about a folding line 123.

The discharge portion 108 may be kept in the position occupied after the subsequent folding operation by an adhesive layer 124, which is capable of repeated releases and adhesions and may conveniently be applied to the contact surface 120 provided by the flap element 121. Alternatively, such an adhesive layer may also be provided, however by the contact surface 119 provided by the outermost protective member in series 117 and 118.

After the subsequent folding to the position shown in FIG. 11 the flap portion 122 is folded about folding line 123 and brought onto contact with a contact surface 125 provided by the back film blank 103 at the proximal section 10 of the discharge portion 108.

The function and handling of the series 117 and 118 of protective members may be the same as explained for the embodiment in FIGS. 1 to 5.

Figure 15:
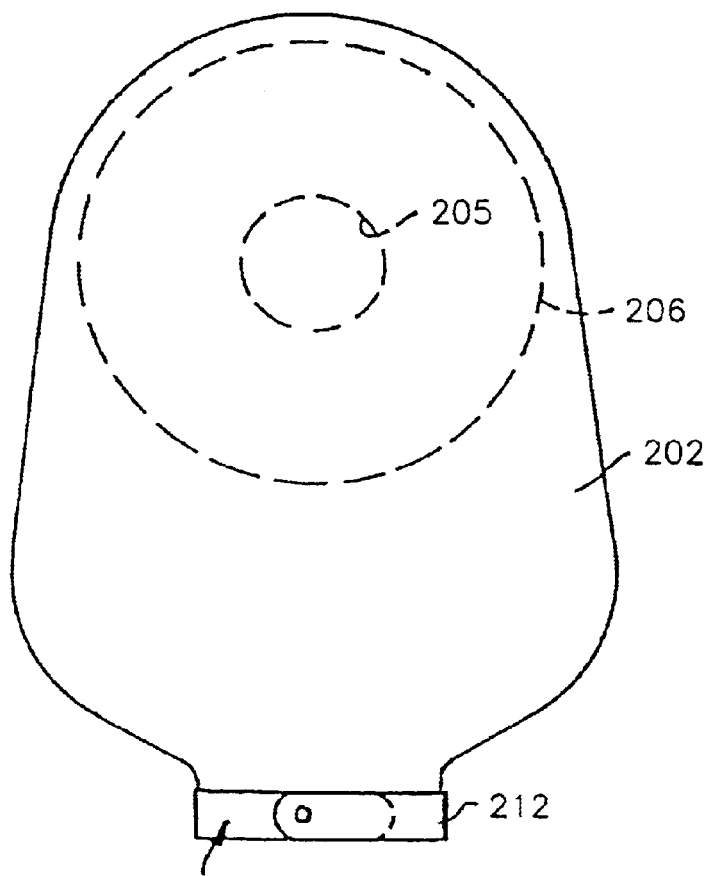
Figure 14:
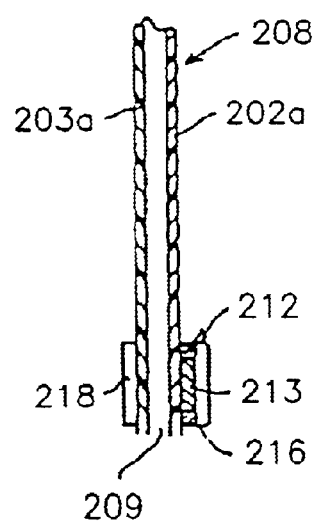

A still further embodiment is shown in FIGS. 13 to 15, in which the discharge opening 209 is provided between the extreme ends of extension 202a and 203a of the front and back film blanks 202 and 203, respectively, of the bag 201, in which the inlet opening 205 in the back film blank 293 is surrounded in this embodiment by a conventional adhesive fixing plate 206. The locking means comprises a strip member 212 firmly connected with the extension 202a of the front film blank 202 at the extreme end thereof.

Such a locking strip is known per se from international patent application WO 96/19164 and comprises a central part 213 adhesively connected with the extension 202a and end sections formed integrally therewith vis folding sections 213a and 213b.

In this case the two series 216 and 218 of peelable, stacked protective members are applied to the external side of the part of the locking strip 212 connected with the extension 202a of the front film blank 202 and the external side of the extension 203a of the back film blank 203. From the cross sectional view in FIG. 14 it will readily appear that folding of the discharge portion 208 from the open position in FIG. 13 to the closed position of use shown in FIG. 15 is effected by folding the discharge portion 208 from the extreme ends of bag extensions 202a and 203a limiting the discharge opening 209 about the locking strip 212. The function of the peelable protective members in each of series 216 and 218 is the same as described above for the embodiments in FIGS. 1 to 5.

As will appear to those skilled in the art the protection of the discharge portion offered by the invention is not limited to the embodiments described in the foregoing, but may be applied to various designs of reusable stoma bags comprising a foldable discharge portion including, in particular the bag designs disclosed in GB 2 000 683 A, U.S. Pat. No. 4,988,343, WO 96/19164 and WO99/66859. The disclosure of the latter, which is incorporated herein by reference, comprises a bag discharge portion provided with resilient sealing plates to improve the sealing of the discharge portion in its closed position. Combined therewith the provision of peelable protective members according to the invention provides the additional advantage of protection of such sealing plates against faecal contamination.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A reusable collecting bag for human body wastes comprising a bag member formed by two film blanks with joined edges, an inlet opening provided in one of said film blanks, connecting elements surrounding said inlet opening for connection of the bag to a body orifice, a narrowed, elongated discharge portion starting at a proximal end at a distance from the inlet opening and extending between two end sections of said film blanks to a distal end, a discharge opening formed in said discharge portion in the vicinity of said distal end, said discharge portion being foldable and unfoldable by at least one folding along a folding line transverse to the longitudinal direction of the discharge portion between said distal and proximal ends to bring the discharge portion from an open unfolded condition to a closed folded condition and vice versa, a locking means for locking the discharge portion in said closed folded condition thereof, and a series of stacked, sequentially peelable protective members adhered to each of two surface sections of the discharge portion at either side of arid adjacent the discharge opening such that removal of each protective member exposes a clean external surface of a next underlying protective member.

2. A reusable collecting bag as claimed in claim 1, wherein the discharge opening is formed between one of said two end sections of the film blanks and an end edge of the other end section as a slit and that said series of protective members are applied to surface sections of said end sections adjoining the end edge of said other end section.

3. A reusable collecting bag as claimed in claim 2, wherein the locking means comprises a locking strip formed integrally with said one end section adjacent to the discharge opening and that one of said series of protective members is applied to the locking strip.

4. A reusable collection bag as claimed in claim 1, wherein said discharge opening is formed as a slit between end edges of both of said end sections and that said series of protective members are applied to external surface sections of each of said end sections adjacent to said slit.

5. A reusable collecting bag as claimed in claim 1, wherein the locking means comprises an adhesive layer applied to at least one of two contact surfaces intended to be brought into contact with each other upon folding of the discharge portion towards the closed position.

6. A reusable collecting bag as claimed in claim 5, wherein said one contact surface, to which an adhesive layer is applied, comprises the side of each of said protective members in at least one of said series facing away from the end section of the discharge portion, to which said one series is applied.

7. A reusable collection bag as claimed in claim 1, wherein the protective members in each of said series are formed as strip members applied to said surface section to extend transverse to the longitudinal direction of the discharge portion.

8. A reusable collection bag as claimed in claim 7, wherein each protective member in each of said series is formed with a gripping flap extending beyond a side edge of the protective member.

9. A reusable collecting bag as claimed in claim 1, wherein each of said series includes from 2 to 8 of said stacked protective members.

10. A reusable collecting bag as claimed in claim 1, wherein said series of stacked peelable protective members are applied to resilient sealing plates connected with said surface sections of the discharge portion.

11. A reusable collecting bag as claimed in claim 1, wherein the protective members are made from materials, which are water soluble or easily degradable.

12. A reusable collecting bag as claimed in claim 1, wherein said protective members have only an inner adhesive surface, said external surface thereof having a sealing layer thereon.

13. A reusable collecting bag as claimed in claim 1, wherein said discharge opening is formed as a slit with a first series of stacked, sequentially peelable protective members adjoining a first side of said slit and a second series of stacked, sequentially peelable protective members adjoining said slit on a second side thereof.

14. A reusable collecting bag as claimed in claim 1, wherein a first series of stacked, sequentially peelable protective members adjoin a first side of said discharge opening and a second series of stacked, sequentially peelable protective members adjoin a second side of said discharge opening, said discharge portion being foldable along said discharge opening to bring said first and second series of protective members into abutment.

15. A reusable collecting bag for human body wastes comprising a bag member formed by two film blanks with joined edges, an inlet opening provided in one of said film blanks, connecting elements surrounding said inlet opening for connection of the bag to a body orifice, a narrowed, elongated discharge portion starting at a proximal end at a distance from the inlet opening and extending between two end sections of said film blanks to a distal end, a discharge opening formed in said discharge portion in the vicinity of said distal end, said discharge portion being foldable and unfoldable by at least one folding along a folding line transverse to the longitudinal direction of the discharge portion between said distal and proximal ends to bring the discharge portion from an open unfolded condition to a closed folded condition and vice versa, a locking means for locking the discharge portion in said closed folded condition thereof, and a series of stacked, sequentially peelable adhesive protective members applied to each of two surface sections of the discharge portion at either side of the discharge opening, said series of stacked peelable protective members being applied to resilient sealing plates connected with said surface sections of the discharge portion.

16. A reusable collecting bag for human body wastes comprising a bag member formed by two film blanks with joined edges, an inlet opening provided in one of said film blanks, connecting elements surrounding said inlet opening for connection of the bag to a body orifice, a narrowed, elongated discharge portion starting at a proximal end at a distance from the inlet opening and extending between two end sections of said film blanks to a distal end, a discharge opening formed in said discharge portion in the vicinity of said distal end, said discharge portion being foldable and unfoldable by at least one folding along a folding line transverse to the longitudinal direction of the discharge portion between said distal and proximal ends to bring the discharge portion from an open unfolded condition to a closed folded condition and vice versa, a locking means for locking the discharge portion in said closed folded condition thereof, and a series of stacked, sequentially peelable adhesive protective members applied to each of two surface sections of the discharge portion at either side of the discharge opening, said discharge opening being formed between one of said two end sections of the film blanks and an end edge of the other end section as a slit and said series of protective members being applied to surface sections of said end sections adjoining the end edge of said other end section.

\* \* \* \* \*